(12) United States Patent
Diermann et al.

(10) Patent No.: US 6,706,009 B2
(45) Date of Patent: Mar. 16, 2004

(54) MICRO PERFUSION DEVICE

(75) Inventors: Ulrich Diermann, Ispach (CH); Ulrich Haueter, Grosshochstetten (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 10/226,104

(22) Filed: Aug. 22, 2002

(65) Prior Publication Data

US 2003/0050593 A1 Mar. 13, 2003

Related U.S. Application Data

(63) Continuation of application No. PCT/CH01/00095, filed on Feb. 13, 2001.

(30) Foreign Application Priority Data

Feb. 25, 2000 (DE) .......................... 100 08 825

(51) Int. Cl.⁷ .......................... A61M 1/00; A61M 5/178
(52) U.S. Cl. .............. 604/33; 604/164.02; 604/164.04; 604/165.02
(58) Field of Search .............. 604/27–30, 31, 604/33, 43, 67, 164.01, 164.02, 164.06, 165.02, 167.01, 167.02, 167.04, 167.06, 167.03; 600/563

(56) References Cited

U.S. PATENT DOCUMENTS

| | | | | |
|---|---|---|---|---|
| 3,081,770 A | * | 3/1963 | Hunter | |
| 4,014,333 A | * | 3/1977 | McIntyre | ............... 128/240 |
| 4,096,860 A | * | 6/1978 | McLaughlin | |
| 4,217,895 A | * | 8/1980 | Sagae et al. | ............. 128/214.4 |
| 4,693,257 A | * | 9/1987 | Markham | ............... 128/752 |
| 5,097,834 A | | 3/1992 | Skrabal | |
| 5,372,582 A | | 12/1994 | Skrabal | |
| 5,669,394 A | * | 9/1997 | Bergey et al. | ............ 128/750 |
| 6,083,202 A | * | 7/2000 | Smith | ................. 604/164 |
| 6,210,379 B1 | * | 4/2001 | Solomon et al. | ......... 604/272 |
| 6,391,007 B2 | * | 5/2002 | Chang et al. | .......... 604/164.01 |

* cited by examiner

*Primary Examiner*—Sharon Kennedy
(74) *Attorney, Agent, or Firm*—Dorsey & Whitney LLP (57) ABSTRACT

A micro perfusion device and method for obtaining at least one constituent of a body fluid. The at least one constituent is obtained using a subcutaneously-positioned perfusion catheter into which perfusate is introduced by a supply channel and an injection needle. The perfusate absorbs the at least one constituent as it flows out of the perfusion catheter and through a discharge channel.

18 Claims, 5 Drawing Sheets

MICRO PERFUSION DEVICE

CROSS-REFERENCE TO RELATED APPLICATION(S)

This is a continuation application of International Patent Application PCT/CH01/00095, filed on Feb. 13, 2001, which claims priority to German Patent Application No. DE 100 08 825 A1, filed on Feb. 25, 2000, both of which are incorporated by reference herein.

BACKGROUND OF THE INVENTION

The invention relates to a micro perfusion device for obtaining at least one constituent of a body fluid by means of a subcutaneously positioned perfusion catheter.

Figure 7:
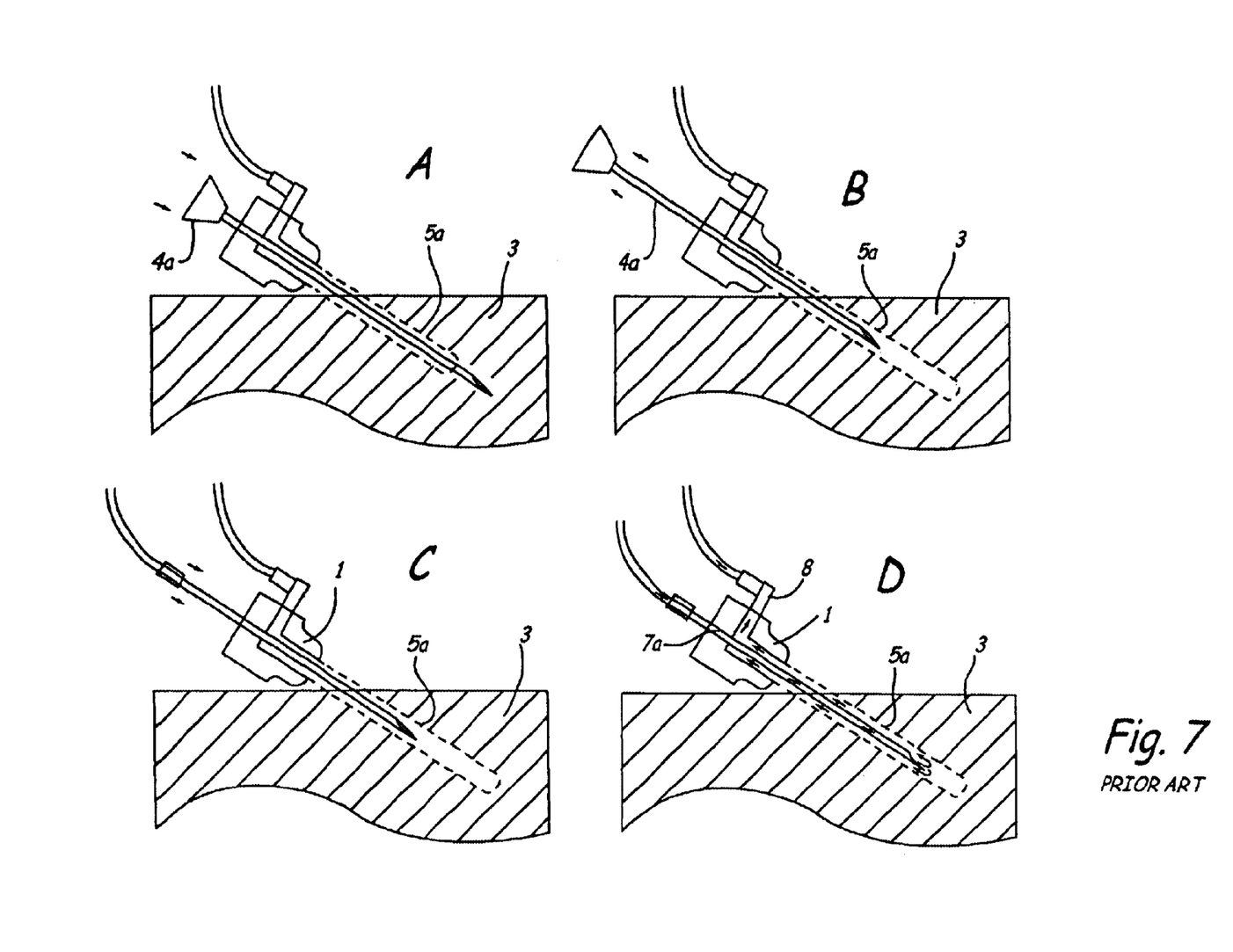
FIG. 7 is a micro perfusion device from the prior art.

FIG. 7D shows a micro perfusion device as described in "Open-Flow Microperfusion . . . ", Z. Trajanoski et al., Diabetes Care, Volume 20, Number 7, July 1997, pages 1114 ff. The device comprises a casing 1 which may be fixed to the skin. A flexible, permeable perfusion catheter 5a projects from the casing 1, said catheter being subcutaneously positioned in a tissue 3. A supply catheter 7a for a rinsing liquid—referred to as perfusate in the following protrudes into the perfusion catheter 5a. The perfusion catheter 5a and the supply catheter 7a form a double-lumen catheter in the tissue 3, comprising an inner lumen within the supply catheter 7a and a surrounding outer lumen between the supply catheter 7a and the perfusion catheter 5a. In the casing 1, the outer lumen feeds into a discharge channel 8 to which a discharge catheter is connected. In order to obtain body fluid from the tissue 3, the perfusate is guided through the supply catheter 7a up close to a front distal end of the perfusion catheter 5a. Once the perfusate has emerged at the front distal of the supply catheter 7a, it flows back along the supply catheter 7a in the outer lumen. A rinsing liquid is used as the perfusate which penetrates the constituent whose concentration in the body fluid is to be ascertained. Furthermore, body fluid is sucked into the outer lumen through the perforated perfusion catheter 5a by the rinsing effect. The mixture of perfusate and body fluid is discharged through the discharge channel 8 to a measuring means. The fluid is conveyed through the device by means of a pump.

The placement procedure prior to the use of the perfusate can be seen from FIGS. 7A to 7D. An injection needle 4a is used to position the device. Before it is positioned, the perfusion catheter 5a tightly surrounds the injection needle 4a. Once the skin has been pierced and the injection needle 4a positioned in the tissue 3 (FIG. 7A), the injection needle 4a is retracted again (FIG. 7B), and the perfusion catheter Sa remains in the tissue in the position shown. The supply catheter 7a is then inserted through the casing 1 into the perfusion catheter 5a (FIG. 7C). It is inserted in the perfusion catheter 5a until it takes up most of the length of the perfusion catheter 5a (FIG. 7D). The front end of the supply catheter 7a is, however, some distance short of the front end of the perfusion catheter 5a.

Micro perfusion devices of the type described require piercing the skin, retracting the injection needle and subsequently providing a perfusate supply.

BRIEF SUMMARY OF THE INVENTION

It is therefore an object of the invention to provide a micro perfusion device which can be easily positioned and operated.

The present invention, in one embodiment, is a micro perfusion device for obtaining at least one constituent of a body fluid using a subcutaneously positioned perfusion catheter comprising a casing, a supply for a perfusate, a hollow injection needle, the perfusion catheter and a discharge channel formed in the casing for discharging the perfusate together with the at least one constituent. The injection needle comprises a front needle opening, distal when subcutaneously positioned, and a rear needle opening. The front needle opening can be formed by a front-facing opening in the conventional way, for example by needle grinding. It can also be formed by a lateral opening in a surface of the injection needle. In one embodiment, the rear needle opening is formed on the rear facing side of the injection needle. It can be formed by a slit or a bore or by laterally cutting the surface area of the injection needle. The injection needle is accommodated by the casing, and may be slid from a front sliding position to a rear sliding position. In its front sliding position, it protrudes through the perfusion catheter. In its rear position, it protrudes into the perfusion catheter, however the perfusion catheter protrudes beyond its front needle opening in the rear position. The injection needle can be a steel needle. Alternatively, other needles can be used as long as they have a sharp tip to cleanly penetrate the skin, are sufficiently rigid for positioning, and are histocompatible.

The injection needle in one aspect of the invention serves to position the perfusion catheter in a tissue whose body fluid and/or from its body fluid the at least one constituent is to be obtained. Alternatively, the injection needle not only fulfills the function of positioning the perfusion catheter, but also fulfills the further function of introducing the perfusate into the perfusion catheter. To this end, a fluid connection from the perfusate supply into the injection needle is formed by the rear needle opening, at least in the rear sliding position of the injection needle. When the device is implanted, i.e. subcutaneously positioned, the perfusate is thus introduced through the perfusate supply, the rear needle opening, the hollow injection needle and finally through its front needle opening into the surrounding perfusion catheter and then rinses the perfusion catheter. Since the injection needle assumes the double function of positioning and introducing the perfusate, the step of subsequently inserting a perfusate supply into the perfusion catheter can be omitted.

According to one embodiment of the present invention, the micro perfusion device can be formed by simply developing catheter heads such as those for infusing insulin within the framework of diabetotherapy. A particularly suitable catheter head is described in DE 198 21 723.4 by the Applicant. The catheter head described therein already comprises an injection needle accommodated slidably in the catheter head casing, with a front and a rear needle opening. The rear needle opening is formed by a lateral opening through which, once an infusion catheter has been positioned, the insulin solution is supplied for the purpose of priming the catheter head. With respect to the injection needle of this catheter head, only a fluid-proof connection is required in the area of the rear needle opening for supplying the perfusate. Furthermore, a discharge channel having a fluid-proof connection to the infusion catheter or perfusion catheter, respectively, has to be formed in the catheter head. As a perfusion catheter, the infusion catheter can be perforated.

The micro perfusion device, in one embodiment, serves to measure or ascertain the glucose concentration in the body fluid in the vicinity of the implanted perfusion catheter. In this case, the at least one constituent of the body fluid is glucose. The body fluid together with the perfusate can be obtained quite simply by the rinsing process. By using an appropriate perfusate or rinsing fluid, a particular constituent can also be selectively obtained by means of the micro perfusion device in accordance with the invention, in addition to the body fluid rinsed with it.

Perfusion, according to one aspect of the present invention, is achieved by suctioning the discharge channel by means of a pump. The perfusate can also be pressed into the injection needle. Alternatively, it can be conveyed by a combination of pressure and suction.

In one embodiment, the fluid connection between the perfusate supply and the injection needle only exists in the rear sliding position of the injection needle. In this case, the perfusate supply is a supply channel formed in the casing. In the rear sliding position, the injection needle opens into this supply channel via its rear needle opening. This ensures that the perfusate discharge in the casing is sealed fluid-proof with respect to the perfusion supply. Appropriate sealing means can be provided in the casing for this purpose.

In another embodiment, the rear needle opening of the injection needle is permanently connected to the perfusate supply. For this purpose, a catheter forming the perfusate supply can very simply be placed over the rear end of the injection needle, which is open-back on its facing side, or otherwise connected fluid-proof to the inner hollow space of the injection needle.

The perfusion catheter can be formed by a catheter closed on its surface side, having only an open front facing side. Alternatively, the perfusion catheter is laterally permeable to the constituent to be measured or, selectively, only for the constituent to be measured or for the body fluid as a whole. The to perfusion catheter can be manufactured from a porous material. If the perfusion catheter is perforated, then the lateral perforation openings of the perfusion catheter can be elongated in the longitudinal direction of the catheter, in order to obtain as great a stability against straining as possible. Straining the catheter as it is inserted into the tissue, also known as peal back effect, is thus prevented or at least kept to a minimum. The perforation openings can be arranged on gaps or offset with respect to each other, not along a line extending in the longitudinal direction of the perfusion catheter but in the circumferential direction of the perfusion catheter. The catheter can be perforated as it is formed, or subsequently, for example using lasers.

In order to obtain a perfusion catheter which is as slim as possible, the outer cross-section of the injection needle and the inner cross-section of the perfusion catheter exhibit different shapes, such that the perfusion catheter only abuts the injection needle in longitudinal strips, and a longitudinal gap remains between adjacent longitudinal strips. In one embodiment, either the injection needle or the perfusion catheter exhibits a cross-section which deviates from the circular form. In this form, the perfusion catheter can wrap tightly around the injection needle along its entire length situated in the tissue. A flow cross-section for the perfusate flowing back nonetheless remains between the outer surface area of the injection needle and the inner surface area of the perfusion catheter. If, for example, the injection needle exhibits an outer cross-section deviating from the circular form along its implanted length, then the perfusion catheter can exhibit a circular inner cross-section tensed around the needle. Equally, the perfusion catheter can exhibit a non-circular inner cross-section and the injection needle a circular outer cross-section. However, it is also possible for the outer cross-section of the injection needle and the inner cross-section of the perfusion catheter to deviate from the circular form, so long as it is ensured that a sufficient flow cross-section for the purpose of rinsing remains between the needle and the perfusion catheter and that the perfusion catheter surrounds the injection needle, in some embodiments the perfusion catheter being wrapped tightly around the injection needle, for the purpose of securely implanting it.

In its rear sliding position, the injection needle is, according to one aspect of the invention, fixed to the casing in such a way that it can be tactilely sensed by someone using the micro perfusion device when the injection needle is in its rear sliding position. The injection needle can simply be moved into its rear sliding position against a stopper. The injection needle can be fixed not only against sliding further, beyond the rear sliding position, but also against the injection needle advancing. The injection needle can be fixed to the casing in its rear sliding position by means of a locking connection, such as a detachable locking connection. For fixing the injection needle, a protrusion, a dent, a slit or the like can be formed on the injection needle. In one embodiment, the rear needle opening is used for the purpose of the locking connection.

In a further embodiment, the micro perfusion device is not only used to obtain the at least one constituent of the body fluid, but simultaneously serves as a miniature measuring means or at least as an electrode platform for a measuring means. The measuring means can serve to measure or ascertain the concentration of the at least one constituent in the body fluid. When used as an electrode platform, an electrode of the measuring means is formed on the lower side of the casing, via which the casing sits on the tissue. A working electrode of the measuring means is electrically connected to the discharged rinsing fluid and can be arranged in the discharge channel of the casing. The electrode formed on the lower side of the casing forms the counter electrode to this working electrode and serves to measure an electrical current and/or an electrical potential. In one aspect of the present invention, a sufficiently large bearing area is formed on the lower side of the casing for the counter electrode to be able to form a sufficiently large contact area with the tissue and simultaneously be used as a reference electrode. Furthermore, it can fulfill an adhesive function, for adhering to the skin.

When it is formed as a miniature measuring means, a sensor is arranged in the casing of the micro perfusion device, the sensor in one aspect of the invention measuring the concentration of the at least one constituent in the body fluid. More precisely, the concentration in the perfusate flowing back is measured and from this, the concentration in the body fluid are ascertained. The sensor can be arranged in an area of the outlet bordering the outer lumen. It can be inserted or recessed into a side wall of the outlet and, in one embodiment, does not protrude out of the wall, in order to keep the flow resistance to a minimum. According to another aspect of the invention, no parts of the casing wall or only as much casing wall as is necessary to securely attach the sensor is arranged in the flow path between the outer lumen and the sensor. The sensor is thus arranged as near to the sampling point as possible, but outside the body.

Although forming it with an integrated sensor, as an electrode platform and as an electrode platform with an integrated sensor are particularly advantageous in combination with the micro perfusion device in accordance with the invention, each of these formations, in particular forming an electrode on the lower side of the casing, can also be realized with all conventional micro perfusion devices.

DETAILED DESCRIPTION

Figure 1A:
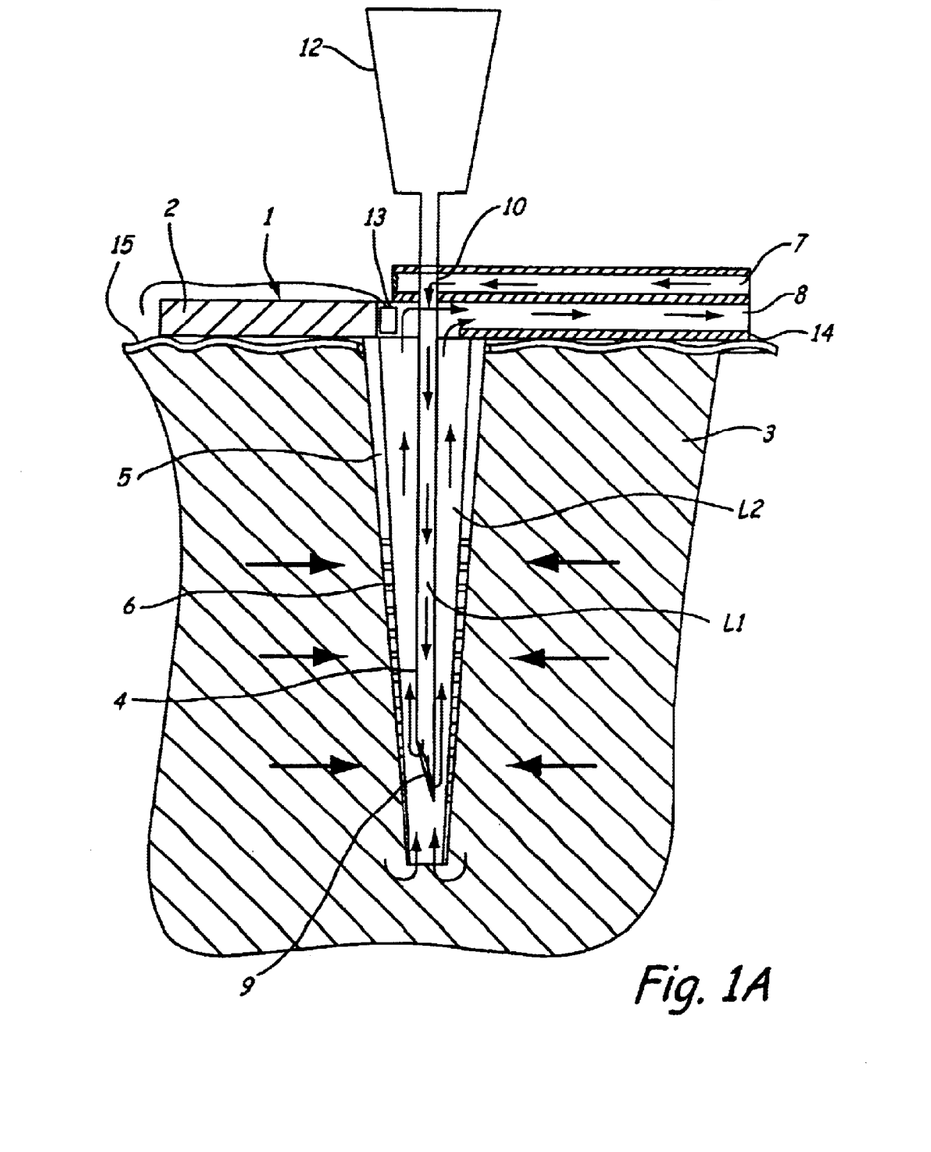
FIG. 1A is a cross-sectional view of a micro perfusion device, according to one embodiment of the present invention.

FIG. 1A shows one embodiment of an implanted micro perfusion device in a longitudinal section. The device comprises a casing 1 with a bearing disc 2, onto the lower side of which an adhesive patch 15 is attached. A flexible, perforated perfusion catheter 5 projects perpendicularly from the lower side of the bearing disc 2. The perfusion catheter 5 concentrically surrounds an injection needle 4 protruding into it. The injection needle 4 is formed in the manner of injection needles such as are known from catheter heads for infusing insulin. The injection needle 4 is formed by a slim, straight hollow cylinder having a front needle opening 9 at its distal, front facing end and a rear needle opening 10 in the surface of the injection needle 4. The injection needle 4 does not comprise any other openings. The injection needle 4 encloses an inner lumen L1 between its two openings 9 and 10. An outer lumen L2, in the form of an annular gap, is formed between the injection needle 4 and the perfusion catheter 5.

In the casing 1, a discharge channel 8 and a perfusate supply lying above it in the form of a supply channel 7 are formed in the bearing disc. The injection needle 4 is accommodated slidably in the casing, guided in a straight line in the longitudinal direction. The linear guide is formed by a through-bore which projects through the casing 1 from an upper side to the opposite lower side. In this way, the injection needle 4 projects through both the supply channel 7 and the discharge channel 8. In the supply channel 7, two sealing rings 11 are inserted into two recesses, each encircling the through-bore in the inner wall of the supply channel 7, said sealing rings 11 surrounding the injection needle 4 in a pressure force seal. In a rear sliding position of the injection needle 4, shown, the rear needle opening 10 comes to rest between the two sealing rings 11. In this way, a fluid connection between the supply channel 7 and the inner lumen L1 is created in the rear sliding position of the injection needle 4, and the supply channel 7 and discharge channel 8 are constantly separated, fluid-proof.

Figure 1B:
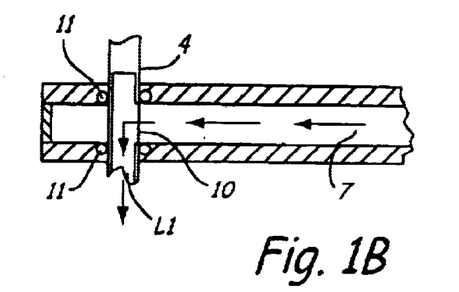
FIG. 1B is a cross-sectional view of a portion of a micro perfusion device, according to one embodiment of the present invention.

In the rear sliding position of the injection needle 4, the sealing rings 11 simultaneously establish a locking connection between the injection needle 4 and the casing 1. In the locking position, i.e. in the rear sliding position, the two sealing rings 11 are pressed into the rear needle opening 10. In this way, a locking or latching effect is achieved. The rear needle opening 10 extends in the longitudinal direction of the injection needle 4 over such a length that both sealing rings 11 come to rest in the rear needle opening 10 and one each of the two sealing rings 11 presses on a rear and a front opening rim, respectively. For providing the locking connection, it would in principle be sufficient if only one of the sealing rings 11 came to rest behind the rear or front rim of the rear needle opening 10, in the rear sliding position. However, pressing against both the rear rim and against the opposite, front opening rim of the rear needle opening 10 creates a locking connection which prevents the injection needle 4 from being unintentionally slid in either sliding direction. The fluid connection between the supply channel 7 and the injection needle 4, as well as the locking connection between the casing 1 and the injection needle 4, are shown again in a separate, enlarged detail in FIG. 1B.

In order to facilitate manually sliding the injection needle 4, the injection needle 4 is provided with a needle grip 12 on its rear end protruding out of the casing 1.

FIG. 1A shows one embodiment of the micro perfusion device in its operational state during micro perfusion, wherein the injection needle 4 is situated in its rear sliding position in the casing 1. Before the perfusion catheter 5 is implanted or positioned in the tissue 3, the injection needle 4 projects through the perfusion catheter 5 in a front sliding position. In this initial state, the tip of the injection needle 4 including the front needle opening 9 lies beyond the front end of the perfusion catheter 5. In this initial state, the needle grip 12 is pressed up against the surface of the casing 1. In order to position the perfusion catheter 5, the injection needle 4 and the perfusion catheter 5, which at least at its front end wraps around the injection needle 4, are pierced through the skin and inserted into the tissue 3, to the position shown in FIG. 1A. In this position, the bearing disc 2 of the casing 1 lies flat on the skin via its lower side. The adhesive patch 15 attached to the lower side of the bearing disc 2 forms an adhesive area with the skin. By pressing the casing 1 against the skin, an adhesive connection is established. In order to perform micro perfusion, the injection needle 4 is retracted to the rear sliding position shown in FIG. 1A, once the casing 1 has been positioned and attached. The micro perfusion device is then ready for micro perfusion to be performed, in order to obtain the at least one constituent of the body fluid.

According to one aspect of the invention, the perfusion catheter 5 is perforated with perforation openings 6 in a surface area between its front distal end and its rear proximal end bordering the casing 1. A non-perforated surface area remains in front of the perforated area at the front end of the perfusion catheter 5. The perfusion catheter 5 is also non-perforated in the area of its rear end. On its facing side, the perfusion catheter 5 opens forwards. When the perfusion catheter 5 is rinsed, so-called open flow micro perfusion arises. A perfusate is guided through a connected supply catheter into the supply channel 7 of the casing 1, enters the hollow injection needle 4 through its rear needle opening 10, flows through the injection needle 4 and emerges into the perfusion catheter 5 through the front distal needle opening 9 at the tip of the needle. Having emerged, the perfusate in the outer lumen L2 between the outer surface of the injection needle 4 and the perfusion catheter 5 flows back towards the casing 1. As the perfusate flows back, body fluid F is sucked in through the perforation openings 6 due to a resultant jet effect in the outer lumen L2 and carried along in the back flow of perfusate, and selectively, the body fluid constituent to be obtained or a number of body fluid constituents are absorbed through the perforation openings 6 due to a concentration gradient between the body fluid F and the perfusate and carried along in the back flow of perfusate. The perfusate flowing back passes from the outer lumen L2 into the discharge channel 8 via a fluid connection formed in the casing 1 and then flows through a discharge catheter connected to the discharge channel 8, into a collecting container. The perfusion catheter 5 is connected fluid-proof to the casing 1.

In the casing 1, a miniature sensor 13 is arranged in a flow cross-section of the perfusate flowing back. The sensor 13 is arranged in the discharge channel 8 in the casing 1. In one embodiment, it is arranged immediately downstream of the perfusion catheter 5. The sensor 13 need not be implanted but rather can be situated in a flow cross-section outside the tissue 3. In one aspect of the present invention, it can be inserted, for example clipped, into the casing 1 at any time, including after the micro perfusion device has been positioned.

The micro perfusion device can serve not only as a sensor platform, but can also serve as an electrode platform for a measuring means. According to one aspect of the invention, a working electrode 14 is formed in the casing 1 on an inner wall of the discharge channel 8 or forms an area of the inner wall. The adhesive patch 15 is itself electrically conductive and is electrically connected to the skin. It serves the measuring means as a counter electrode to the working electrode 14. The bearing area of the adhesive patch 15 is, in one aspect of the present invention, sufficiently large that it also simultaneously forms a reference electrode.

Figure 2:
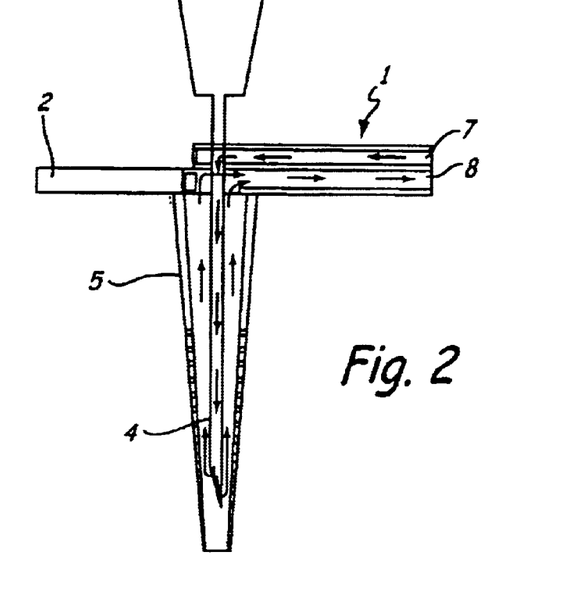
FIG. 2 is a cross-sectional view of a micro perfusion device having no sensors or electrodes, according to one embodiment of the present invention.

FIG. 2 shows a micro perfusion device according to another embodiment. The device does not have an integrated sensor or integrated electrodes. When using the device, the sensor and the electrodes of the measuring means are to be arranged in other known ways.

Figure 3A:
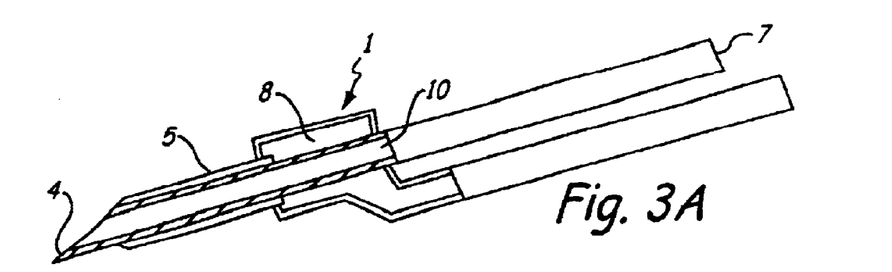
FIG. 3A is a cross-sectional view of a micro perfusion device before it is positioned in the tissue, according to one embodiment of the present invention.
Figure 3B:
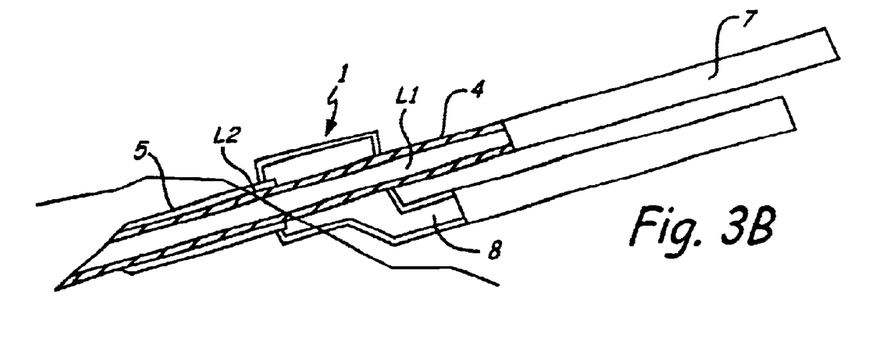
FIG. 3B is a cross-sectional view of a micro perfusion device in its rear sliding position, according to one embodiment of the present invention.

FIG. 3A and FIG. 3B show an alternative micro perfusion device having a perfusate supply 7 formed by a supply catheter 7 which is directly and permanently connected to the injection needle 4. Via its rear needle opening 10, the injection needle 4 has a permanent fluid connection to the supply catheter 7. Thus, the injection needle 4 is linearly guided in the casing 1 and the perfusate supplied separately from each other. When the injection needle 4 is retracted into its rear sliding position, the supply catheter 7 is moved along with the injection needle 4.

FIG. 3A shows a micro perfusion device in its initial state before it is positioned in the tissue, the injection needle 4 assuming its front sliding position with respect to the casing 1 and the perfusion catheter 5. The micro perfusion device is also still in this state after it has been positioned in the tissue, until the injection needle 4 is retracted to its rear sliding position. A cut-off valve or slide (not shown) is arranged in a flow cross-section of the supply catheter 7, so that the supply of perfusate to the injection needle 4 can be interrupted until perfusion.

FIG. 3B shows the injection needle 4 in its rear sliding position. By retracting the injection needle 4 some distance behind the front end of the perfusion catheter 5, a suitable co-axial flow system is created for the subsequent perfusion, comprising the lumen L1 enclosed by the injection needle 4 and the outer lumen L2 formed as an annular space between the injection needle 4 and the perfusion catheter 5. The outer lumen L2 has a fluid connection to the discharge channel 8, again formed in the casing 1, a discharge catheter being connected to said discharge channel 8. With respect to the other structural features and functionality, the embodiments of the first example embodiment apply.

Figure 4A:
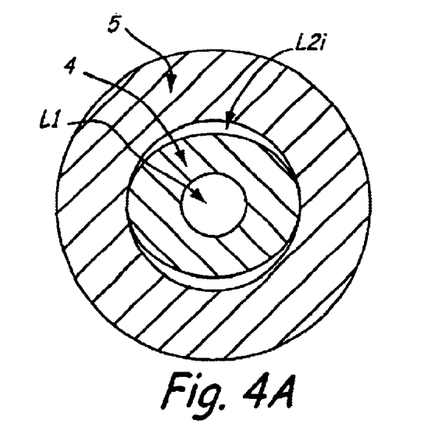
FIG. 4A is a cross-sectional view of an injection needle with a non-circular out cross-section, according to one embodiment of the present invention.
Figure 4B:
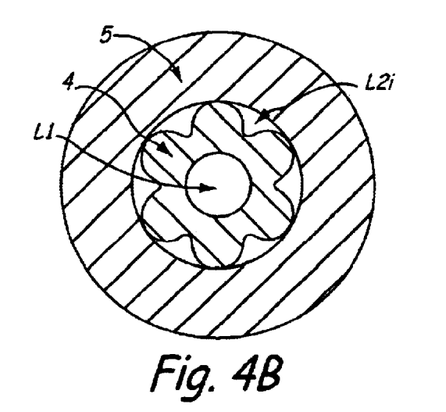
FIG. 4B is a cross-sectional view of an injection needle with a non-circular out cross-section, according to one embodiment of the present invention.
Figure 4C:
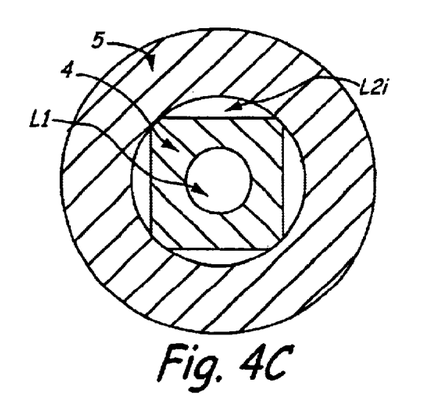
FIG. 4C is a cross-sectional view of an injection needle with a non-circular out cross-section, according to one embodiment of the present invention.
Figure 5A:
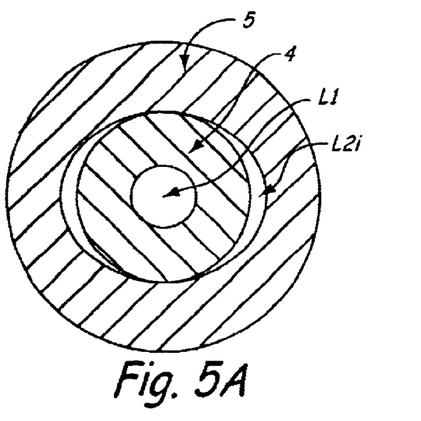
FIG. 5A is a cross-sectional view of a perfusion catheter with a non-circular inner cross-section, according to one embodiment of the present invention.
Figure 5B:
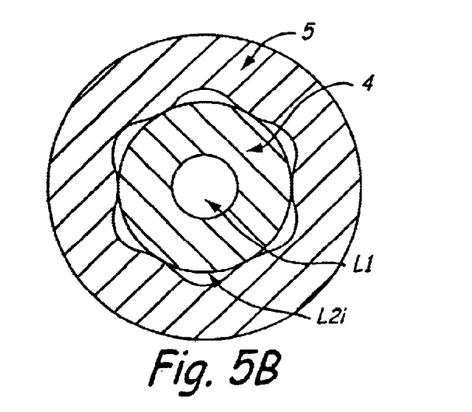
FIG. 5B is a cross-sectional view of a perfusion catheter with a non-circular inner cross-section, according to one embodiment of the present invention.
Figure 5C:
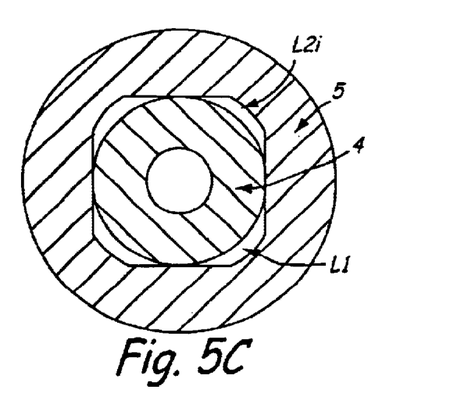
FIG. 5C is a cross-sectional view of a perfusion catheter with a non-circular inner cross-section, according to one embodiment of the present invention.

FIGS. 4A–4C and 5A–5C are cross-sections of alternative embodiments of injection needles 4 and perfusion catheters 5. The cross-sectional shapes are adapted such that a sufficient flow cross-section always remains in the outer lumen L2 over the entire flow length of the fluid flowing back, and the perfusion catheter 5 nonetheless tightly surrounds or wraps around the injection needle 4. In FIGS. 4A–4C, the inner cross-section of each alternative perfusion catheter 5 is circular in its neutral, untensed state, while the outer cross-section of each alternative injection needle 4 deviates from the circular cross-sectional shape. In the cross-section combinations in FIGS. 5A–5C, by contrast, the outer cross-section of each alternative injection needle 4 is circular, and the inner cross-section of each alternative perfusion catheter 5 deviates from the circular form.

When installed, the perfusion catheter 5 in one aspect of the invention is also tensed around the injection needle 4 in its neutral state. In this way, partial lumens L2$i$ through which the perfusate can flow back are formed along and distributed around the injection needle 4, between the points at which the perfusion catheter 5 presses on the injection needle 4. By forming the outer cross-section of the injection needle 4 and the inner cross-section of the perfusion catheter 5 such that the perfusion catheter 5 only presses on the injection needle 4 in longitudinal strips and partial lumens 2L$i$ remain between the pressure strips, the perfusion catheter 5 can be tensed around the injection needle 4 over its entire implanted length or at least over a front, partial length. The injection needle 4 thus supports the perfusion catheter 5, which is advantageous when piercing the skin and inserting it further into the tissue.

Figure 6:
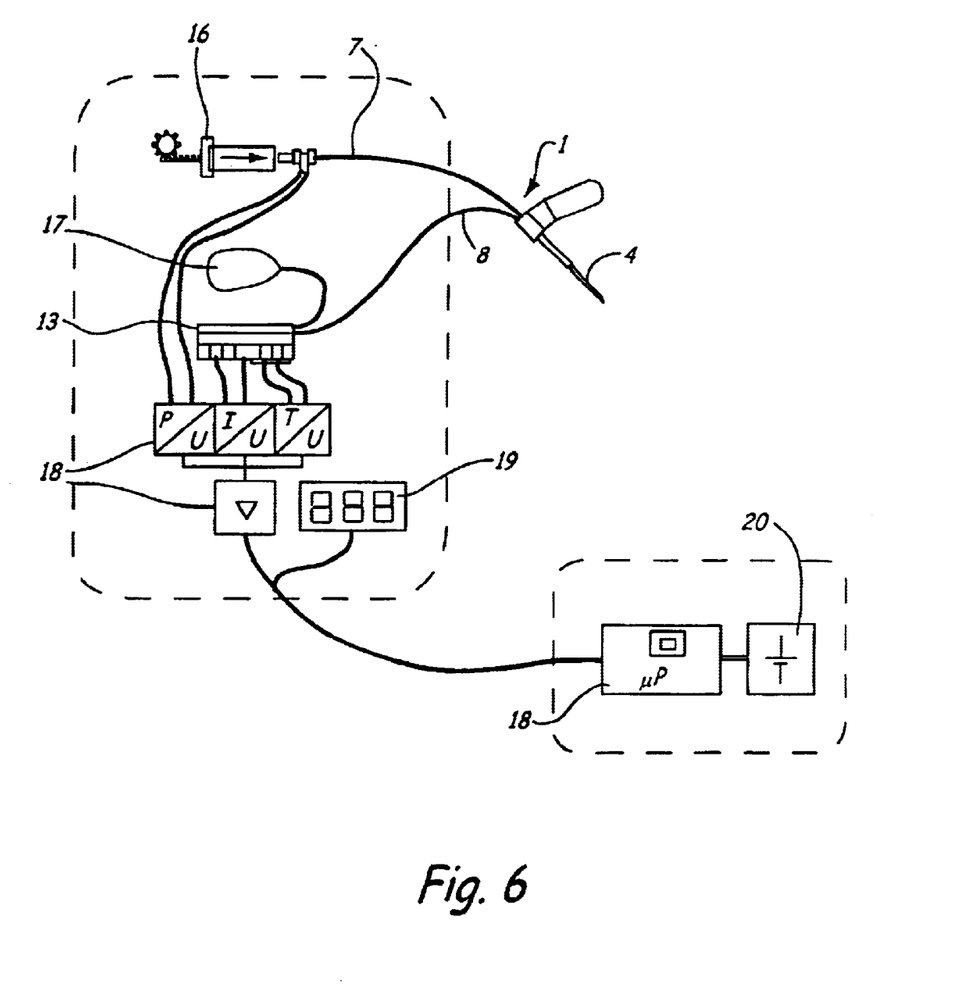
FIG. 6 is a schematic drawing of a micro perfusion system with a measuring and evaluating means.

FIG. 6 shows a schematic drawing of a perfusion device comprising a connected measuring and evaluating means. The micro perfusion device is connected to a supply catheter 7 and a discharge catheter 8. A micro pump 16 conveys a perfusate through the supply catheter 7 into the injection needle 4. The perfusate flowing back is supplied to the external sensor 13 and then guided to a collecting container 17 and disposed of. The perfusate flowing back to the sensor 13 contains the at least one constituent, whose concentration is to be ascertained by measurement. If this constituent is glucose, then the sensor 13 is a glucose sensor. The measuring signals from the sensor 13 are supplied to an evaluation means 18 which ascertains the concentration of the at least one constituent from them and displays this on a display 19. In one embodiment, the micro perfusion device is positioned in the tissue of the lower arm. The micro pump 16, the sensor 13, the collecting container 17, a part of the evaluation means 18 and the display 19 can be collectively accommodated in a lower arm unit. A microprocessor of the evaluation means 18 and a battery 20 can be accommodated together in a belt unit and connected to the lower arm unit in order to exchange data and supply the lower arm unit with power. The evaluation unit 18, in particular the microprocessor, not only evaluates the measuring signals from the sensor 13 but also controls the micro pump 16. Alternatively, the sensor 13 is not arranged in an external lower arm unit but is rather integrated in the casing 1 of the device.

In the foregoing description, embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

Although the present invention has been described with reference to preferred embodiments, persons skilled in the art will recognize that changes may be made in form and detail without departing from the spirit and scope of the invention.

We claim:

1. A micro perfusion device for obtaining at least one constituent of a body fluid using a subcutaneously positioned perfusion catheter, the device comprising:
   a) a casing;
   b) the perfusion catheter projecting from the casing;
   c) a hollow injection needle slideably disposed within the perfusion catheter in a position ranging from a front sliding position to a rear sliding position, the injection needle in the front sliding position being configured to protrude from a distal end of the perfusion catheter such that a distal end of the injection needle is external to the perfusion catheter;
   d) a supply channel fluidly connected to the injection needle in the rear sliding position through a rear needle opening in the injection needle, the rear sliding position being configured to allow a perfusate to flow from the supply channel through the injection needle and into the perfusion catheter, wherein the supply channel comprises two sealing rings encircling the injection needle, the two sealing rings configured to releasably lock the injection needle into the rear sliding position; and
   e) a discharge channel formed in the casing, the discharge channel being connected to the perfusion catheter for discharging the perfusate.

2. The micro perfusion device of claim 1 wherein the two sealing rings releasably lock the injection needle into the rear sliding position by being partially disposed within the rear needle opening of the injection needle when the injection needle is in the rear sliding position.

3. The micro perfusion device of claim 1, further comprising a sensor configured to provide information regarding the at least one constituent of the body fluid.

4. The micro perfusion device of claim 3, wherein the sensor is disposed within the casing in the discharge channel.

5. The micro perfusion device of claim 3, wherein the sensor is external to the device.

6. The micro perfusion device of claim 5, further comprising:
   (a) a supply catheter fluidly connected to the supply channel;
   (b) an external micro pump forcing the perfusate through the supply catheter and the supply channel and into the injection needle;
   (c) a discharge catheter fluidly connected to the discharge channel, the discharge catheter configured to transport the perfusate to the sensor;
   (d) a collecting container configured to collect the perfusate for disposal; and
   (e) an evaluation component electronically connected to the sensor, the evaluation component configured to ascertain information regarding the at least one constituent and display the information on a display.

7. The micro perfusion device of claim 6, further comprising:
   (a) a microprocessor for the evaluation component, the microprocessor located on a belt separate from the device located on the arm of the patient; and
   (b) a battery configured to provide power to the device, the battery located on the belt.

8. The micro perfusion device of claim 1, further comprising a working electrode configured to provide information regarding the at least one constituent of the body fluid.

9. The micro perfusion device of claim 8, wherein the working electrode is located within the casing on an inner wall of the discharge channel, wherein an adhesive patch on a lower side of the casing is configured to serve as a counter electrode to the working electrode.

10. A micro perfusion device for obtaining at least one constituent of a body fluid using a subcutaneously positioned perfusion catheter, the device comprising:
    a) a casing;
    b) a perfusate supply;
    c) a hollow injection needle configured to protrude through the casing and having a front needle opening and a rear needle opening, the injection needle configured to be slideable from a front sliding position in which the needle protrudes beyond a distal end of the perfusion catheter to a rear sliding position in which the front needle opening is disposed within the perfusion catheter, wherein
    d) the rear needle opening forms a fluid connection from the perfusate supply to the injection needle at least in the rear sliding position of the injection needle, the perfusion catheter projects from the casing and generally surrounds the injection needle, a discharge channel is formed in the casing, the discharge channel being fluidly connected to the perfusion catheter for discharging a perfusate, and the perfusion catheter comprises a catheter surface permeable to the at least one constituent.

11. The micro perfusion device of claim 10, wherein perforation openings of the perfusion catheter are longer in the longitudinal direction of the perfusion catheter than in the circumferential direction of the perfusion catheter.

12. A micro perfusion device for obtaining at least one constituent of a body fluid using a subcutaneously positioned perfusion catheter, the device comprising:
    a) a casing;
    b) a perfusate supply:
    c) a hollow injection needle configured to protrude through the casing and having a front needle opening and a rear needle opening, the injection needle configured to be slideable from a front sliding position in which the needle protrudes beyond a distal end of the perfusion catheter to a rear sliding position in which the front needle opening is disposed within the perfusion catheter, wherein d) the rear needle opening forms a fluid connection from the perfusate supply to the injection needle at least in the rear sliding position of the injection needle, the perfusion catheter projects from the casing and generally surrounds the injection needle, a discharge channel is formed in the casing, the discharge channel being fluidly connected to the perfusion catheter for discharging a perfusate, and the rear needle opening is formed in a surface area of the injection needle and wherein the injection needle is slideably locked into the rear sliding position by a sealing ring removeably locked into the rear needle opening.

13. A micro perfusion device for obtaining at least one constituent of a body fluid using a subcutaneously positioned perfusion catheter, the device comprising:

a) a casing;

b) a perfusate supply;

c) a hollow injection needle configured to protrude through the casing and having a front needle opening and a rear needle opening, the injection needle configured to be slideable from a front sliding position in which the needle protrudes beyond a distal end of the perfusion catheter to a rear sliding position in which the front needle opening is disposed within the perfusion catheter, wherein d) the rear needle opening forms a fluid connection from the perfusate supply to the injection needle at least in the rear sliding position of the injection needle, the perfusion catheter projects from the casing and generally surrounds the injection needle, a discharge channel is formed in the casing, the discharge channel being fluidly connected to the perfusion catheter for discharging a perfusate, and a sensor configured to measure the concentration of the at least one constituent is disposed within the discharge channel.

14. A micro perfusion device for obtaining at least one constituent of a body fluid using a subcutaneously positioned perfusion catheter, the device comprising:

a) a casing;

b) a perfusate supply;

c) a hollow injection needle configured to protrude through the casing and having a front needle opening and a rear needle opening, the injection needle configured to be slideable from a front sliding position in which the needle protrudes beyond a distal end of the perfusion catheter to a rear sliding position in which the front needle opening is disposed within the perfusion catheter, wherein d) the rear needle opening forms a fluid connection from the perfusate supply to the injection needle at least in the rear sliding position of the injection needle, the perfusion catheter projects from the casing and generally surrounds the injection needle, a discharge channel is formed in the casing, the discharge channel being fluidly connected to the perfusion catheter for discharging a perfusate, and a measuring means for measuring the concentration of the at least one constituent comprises a working electrode and a counter electrode, wherein the counter electrode is formed on a lower side of the casing, the lower side contacting a tissue surface once the device has been positioned.

15. A micro perfusion device for obtaining at least one constituent of a body fluid using a subcutaneously positioned perfusion catheter, the device comprising:

a) a casing;

b) a perfusate supply;

c) a hollow injection needle configured to protrude through the casing and having a front needle opening and a rear needle opening, the injection needle configured to be slideable from a front sliding position in which the needle protrudes beyond a distal end of the perfusion catheter to a rear sliding position in which the front needle opening is disposed within the perfusion catheter, wherein d) the rear needle opening forms a fluid connection from the perfusate supply to the injection needle at least in the rear sliding position of the injection needle, the perfusion catheter projects from the casing and generally surrounds the injection needle, a discharge channel is formed in the casing, the discharge channel being fluidly connected to the perfusion catheter for discharging a perfusate, and a measuring means for measuring the concentration of the at least one constituent comprises a working electrode and a counter electrode, wherein the working electrode is formed in the discharge channel.

16. A method of obtaining at least one constituent of a body fluid, comprising:

(a) providing a hollow injection needle slideably disposed in a casing, the casing being configured to be placed against skin of a patient;

(b) providing a perfusion catheter configured to encompass the injection needle;

(c) inserting the perfusion catheter into a tissue containing the at least one constituent when a distal end of the injection needle is protruding from a distal end of the perfusion catheter;

(d) retracting the injection needle until a fluid connection is established between a supply channel and the injection needle;

(e) causing perfusate to flow through the supply channel and the injection needle and out of a distal opening in the injection needle into a lumen between the injection needle and the perfusion catheter;

(f) absorbing the at least one constituent from the body fluid into the perfusate through openings in the perfusion catheter, wherein the at least one constituent is pulled into the lumen across a concentration gradient created as the perfusate is guided away from the distal opening in the injection needle; and (g) causing the perfusate and the at least one constituent to flow out of the lumen through a discharge channel.

17. The method of claim 16, further comprising providing a sensor to ascertain information about the at least one constituent, the sensor being placed downstream of the perfusion catheter.

18. The method of claim 16, further comprising providing a working electrode in the discharge tunnel and providing a counter electrode to the working electrode.

* * * * *